United States Patent
Fuchs

[11] Patent Number: 5,941,700
[45] Date of Patent: Aug. 24, 1999

[54] SUPPORT FOR FIRING ARTICLES IN A DENTAL LABORATORY

[76] Inventor: Theo Fuchs, St. -Gallus-Strasse 35/1, D-78086 Brigachtal, Germany

[21] Appl. No.: 08/997,762

[22] Filed: Dec. 24, 1997

[30] Foreign Application Priority Data

Dec. 24, 1996 [DE] Germany ............................ 196 54 385

[51] Int. Cl.⁶ .................................................... F27D 5/00
[52] U.S. Cl. .......................... 432/258; 432/253; 432/261; 269/305; 269/900; 269/266
[58] Field of Search ..................... 432/253, 258, 432/259, 261; 269/305, 900, 54.5, 266; 248/220.31

[56] References Cited

U.S. PATENT DOCUMENTS

| | | | |
|---|---|---|---|
| 4,184,840 | 1/1980 | Gamberg et al. | 432/253 |
| 4,771,162 | 9/1988 | Schatz et al. | 219/400 |
| 5,326,086 | 7/1994 | Radencic | 269/54.5 |
| 5,467,972 | 11/1995 | Lee et al. | 269/900 |
| 5,752,821 | 5/1998 | Jo | 432/258 |

FOREIGN PATENT DOCUMENTS

| | | | |
|---|---|---|---|
| 2 665 816 | 2/1992 | France | H05K 3/22 |
| 44 28 282 A1 | 2/1996 | Germany | F27B 17/02 |

OTHER PUBLICATIONS

Phoenix Dental Catalog 1982/83.

*Primary Examiner*—Teresa Walberg
*Assistant Examiner*—Jiping Lu
*Attorney, Agent, or Firm*—Pendorf & Cutliff

[57] ABSTRACT

A support for firing articles for a dental laboratory as described, in which a tensioning plate (14) is provided between two carrier plates (10, 12), the carrier plates (10, 12) and the tensioning plate (14) exhibiting a corresponding pattern of boreholes (16). In these boreholes (16) carrier pins (32) are introduced, which by displacement of the tensioning plate (14) with respect to the carrier plates (10, 12) are clamped in place and fixed in their position.

9 Claims, 2 Drawing Sheets

SUPPORT FOR FIRING ARTICLES IN A DENTAL LABORATORY

BACKGROUND OF THE INVENTION

1. Field of the Invention

The invention concerns a support for firing articles in a dental laboratory.

2. Description of the Related Art

In a dental laboratory supports are used in the firing of ceramic articles such as crowns or bridges, upon which support the article being fired is supported during the firing process. Known supports for firing articles are comprised of a carrier plate of a non-oxidizing metal or a ceramic material, in which boreholes are provided in a modular grid or pattern. In the boreholes carrier pins are inserted, which support the article to be fired. Since the articles to be fired in many cases, for example, in the case of bridges or molar crowns, are supported by multiple carrier pins, it is necessary that the height with which the carrier pins project above the carrier plate be adjusted to correspond to the shape of the article to be fired. The height positioning of the carrier pin is determined using fingertip sensitivity and is accordingly not precise. Further, it is known to provide the carrier pin with a flange via which the inserted carrier pin is supported on the carrier plate. Since in this case the carrier pins have a fixed position on the carrier plate, it is necessary for height adjustment that the carrier pins are shortened. This is a time consuming and thus expensive process. Besides this, inaccuracies and imprecision are unavoidable. Imprecision in the height of the carrier pin means and incomplete supporting of the article being fired, which can lead to a bending of the article being fired during the firing process.

The invention is concerned with the task, of providing a carrier for articles being fired, which makes possible a simple and rapid adjustment of the carrier pins with high precision.

SUMMARY OF THE INVENTION

The basic idea of the present invention is comprised therein, of providing a tensioning plate on the carrier plate, which has a pattern which is in registry with the borehole pattern of the carrier plate. As long as the boreholes of the carrier plate and the tensioning plate are superimposed, the carrier pins can be inserted into these boreholes and their position can be adjusted. Then the tensioning plate and the carrier plate are displaced with respect to each other, so that the carrier pins are clamped securely in place in the boreholes by the displacement of the bores of the tensioning plate with respect to the carrier plate.

In a preferred embodiment two carrier plates are envisioned, which are identical in size and pattern of the boreholes. Between these two carrier plates the tensioning plate is situated. For displacement of the tensioning plate a tensioning cam is preferably employed, which is provided rotatably in the carrier plates and which engages the tensioning plate with its cam circumference. The tensioning device can in this manner be actuated with a simple manipulation by pivoting of the tensioning cam and then again be released. The cam circumference of the tensioning cam which engages the tensioning blade is so constructed or designed that the tensioning cam is self-locking or self-restraining in any of its respective tensioning positions. The tensioning plate thus without additional measures remains in the tensioned position necessary for the firing operation.

The support for firing articles is constructed in a simple manner, since it is comprised of only two or, as the case may be, three plates of a non-oxidizing metal with the necessary boreholes and a tensioning cam. The carrier pins are simple cylindrical metal pins. Since the carrier pins need not be shortened for height adjustment, rather only need be clamped into their respective positions, these carrier pins are re-useable multiple times.

The support for firing articles is simple in its operation and permits a rapid and very precise positioning of the carrier pins.

For this the articles to be fired are provided upon the carrier plate and fixed in their firing position with a spacer, for example an adhesive wax. In the released tensioning device, the carrier pins are inserted in the boreholes from the backside. Then the carrier for firing articles is inverted, so that the article to be fired is situated below the carrier plate. The carrier pins fall on the basis of their own weight downwards in the boreholes and are seated exactly and tension free upon the article to be fired. In this position the tensioning device is engaged, so that the carrier pins are clamped and fixed in this exact position. The carrier for firing articles can then be reverted to its normal orientation and the article to be fired can be seated upon the carrier pins after removal of the spacer and be fired in a conventional manner.

BRIEF DESCRIPTION OF THE DRAWINGS

In the following the invention will be described in greater detail by reference to the illustrative embodiment shown in the drawings. There is shown FIG. 1 a perspective view of the support for firing articles, FIG. 2 a partial sectional side view of the support for firing articles, FIG. 3 top view of the support for firing articles and FIG. 4 enlarges the top view X from FIG. 3 without the upper carrier plate.

DETAILED DESCRIPTION OF THE INVENTION

Figure 1:
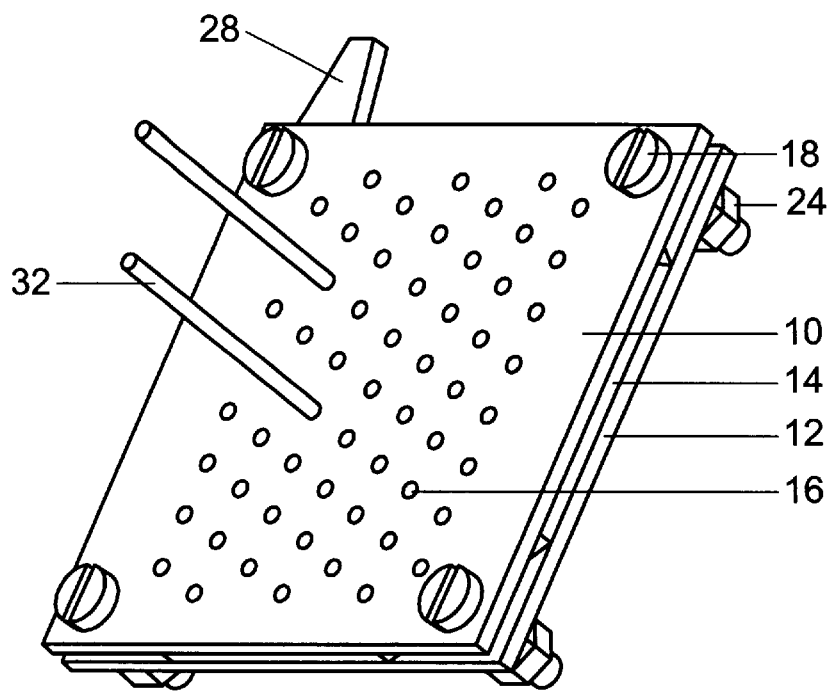
Figure 2:
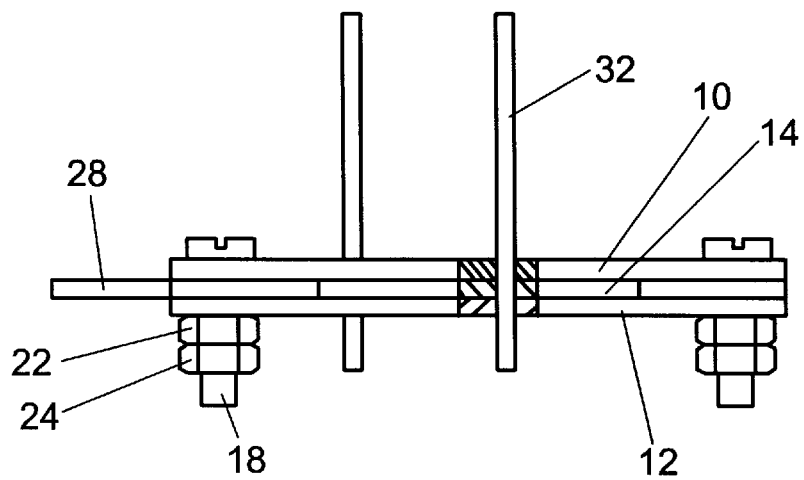
Figure 3:
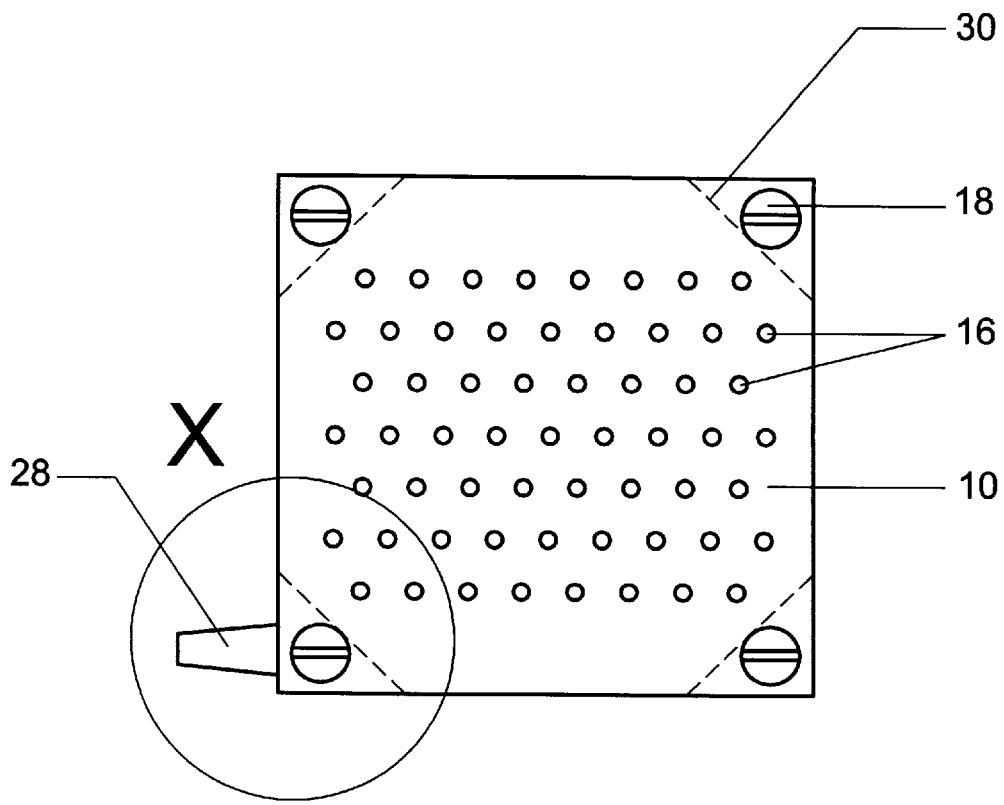
Figure 4:
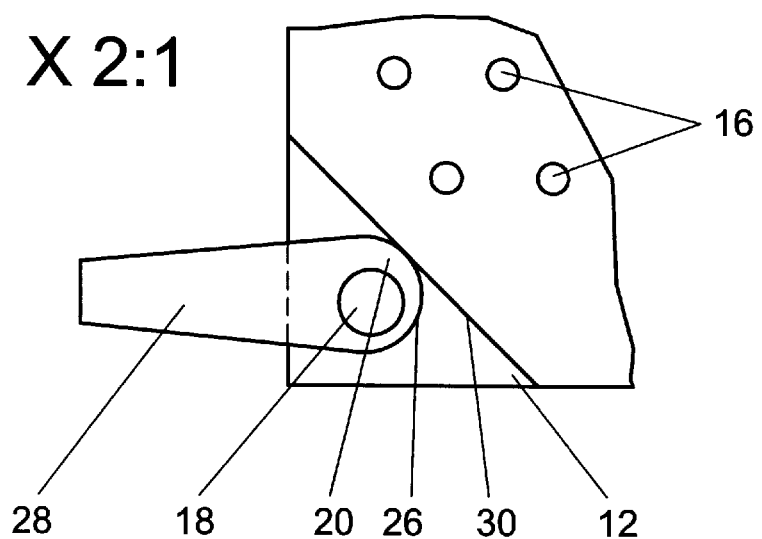

The support for firing articles is comprised of a first carrier plate 10, a second carrier plate 12 and a tension plate 14 oriented between these in a sandwich-like manner. The carrier plates 10 and 12 and the tension plate 14 are comprised of a nonoxidizing steel sheet. The carrier plates 10 and 12 have the same right angled shape and exhibit a corresponding superimposed pattern of through-going boreholes 16, which extend in a pattern over the entire surface of the carrier plates 10 and 12. The tensioning plate 14 provided between the carrier plates 10 and 12 exhibits the same right angled shape as the carrier plates 10 and 12, is however beveled in its four corners, so that the two carrier plates 10 and 12 project at their corners beyond the tensioning plate 14.

The carrier plates 10 and 12 are connected with each other by screws 18 at their four corners in the respective areas projecting beyond the tensioning plate 14. On the screws 18 there are screwed respectively nuts 22 and counter-nuts 24, so that the carrier plates 10 and 12 and the tensioning plate 14 provided therebetween are secured between the head of the screws 18 and the nuts 22 and lock-nuts 24, the plates contacting each other without pressure, and are so maintained. The screws 18 lie against the beveled corner edges 30 of the tensioning plate 14 at three corners and guide these between the carrier plates 10 and 12, so that the tensioning plate 14 is maintained in registry with the carrier plates 10 and 12 and is slidable with respect to these. The tensioning plate 14 likewise exhibits a pattern of through-going boreholes 16 which is identical with the pattern of the bores 16 in the carrier plates 10 and 12 and is held in registry with these by the screws 18 lying at the edge corners 30.

On the fourth corner a tensioning cam 20 is pivotably mounted upon the screw 18 between the carrier plates 10 and 12. The tensioning cam lies with its cam circumference 26 on the edge corner 30 of the tensioning plate 14. The radius of the cam circumference 26 increases in the pivoting direction, that is, slightly increasing in the circumference direction, wherein this increase is so small, that the tensioning cam is self restrainingly maintained in its respective tensioning positions. An operating lever 28 formed on the tensioning cam 20 makes possible the pivoting of the tensioning cam 20.

The support for firing articles is utilized in the following manner:

In the released position of the tensioning cam 20 this exerts no pressure upon the corner edge 30 of the tensioning plate 14. The tensioning plate 14 is therewith maintained via the screws 18 in such a position between the carrier plates 10 and 12, that the pattern of the boreholes 16 of the carrier plates 10 and 12 and the tensioning plate 14 come into exact correspondence. The boreholes 16 thus go axially in alignment through the first carrier plate 10, the tensioning plate 14 and the second carrier plate 12.

The article to be fired, for example a bridge, is provided in the area of the pattern of the boreholes 16 on the first carrier plate 10 and positioned with the desired spacing from the first carrier plate 10 by a spacer, for example adhesive wax. The carrier for the article to be fired is now inverted, so that the first carrier plate 10 is oriented with the thereupon fixed article to be fired situated on the bottom. Now from the back side, that is, from above the carrier, pins 32 are introduced through the two carrier plates 12 of which pins the outer diameter corresponds to the inner diameter of the boreholes 16, so that the carrier pins 32 slide into the boreholes 16 with almost no play. The carrier pins 32 fall through the boreholes 16 of the second carrier plate 12, the tensioning plate 14 and the first carrier plate 10 and are seated loosely, free of tension and in exact position on the article to be fired. Now the tensioning cam 20 is pivoted via the operating lever 28. Thereby the increasing cam circumference 26 presses against the edge corner 30 of the tensioning plate 14 in order that this is displaced with respect to the carrier plates 10 and 12. Since in this displacement of the tensioning plate 14 with respect to the carrier plates 10 and 12 also the pattern of the boreholes 16 of the tensioning plate 14 is displaced with respect to the pattern of the boreholes 16 in the carrier plates 10 and 12, there is caused a slight displacement of the tensioning plate 14, which corresponds to the play of the carrier pins 32 in the boreholes 16, so that the carrier pins 32 are clamped securely in the boreholes 16 and are fixed in their position. The self-locking effect of the cam circumference 26 causes the tensioning cam 20 to remain fixed in the position in which it tensions the carrier pins 32, even if the operating lever 28 is released. Since even a minimal displacement of the tensioning plate 14 by means of the tensioning cam 20 is sufficient for clamping of the carrier pins 32, the screws 18 lying on the other edge corners 30 of the tensioning plate 14 can elastically give way for displacement of the tensioning plate 14. The elastic pressure of the screws 18 upon the tensioning plate 14 further enhances the self-locking of the tensioning cam 20. After the tensioning and fixing of the carrier pins 32 the support for the article to be fired is again reverted and the spacer is removed. The article to be fired is now supported in the exact position by the carrier pins 32 and can be fired in the conventional manner.

After ending of the process and after the removal of the fired article the tensioning device is again released, in which the tensioning cam 20 is again pivoted back by means of the operating lever 28. The elasticity of the screws 18 press the tensioning plate 14 again in the position, in which its boreholes 16 exactly are in register with the boreholes of the carrier plates 10 and 12. The carrier pins 32 are thereby set free and can again fall freely out of the support for articles to be fired and are ready for utilization in the next process.

| LEGEND | |
|---|---|
| 10 | First Carrier Plate |
| 12 | Second Carrier Plate |
| 14 | Tensioning Plate |
| 16 | Boreholes |
| 18 | Screws |
| 20 | Tensioning Cam |
| 22 | Nuts |
| 24 | Lock-Nuts |
| 26 | Cam Circumference |
| 28 | Operating Lever |
| 30 | Edge Corners |
| 32 | Carrier Pins |

What is claimed is:

1. Support for firing articles, said support comprising:
   a carrier plate, said carrier plate provided with boreholes arranged in a pattern, said boreholes adapted for receiving carrier pins;
   a plurality of carrier pins;
   a tensioning plate (14) provided flush against said carrier plate (10) and slideably displaceable with respect to the carrier plate (10), said tensioning plate being provided with boreholes (16) in a pattern which corresponds with the pattern of the boreholes of the carrier plate (10); and
   a tensioning device (20, 26), via which the tensioning plate (14) can be displaced with respect to the carrier plate (10) for clamping of the carrier pins (32) and maintained in its displaced position.

2. Support for firing articles according to claim 1, wherein the tensioning plate (14) is provided between two carrier plates (10 and 12) which are connected to each other in congruence and which exhibit congruent patterns of boreholes (16).

3. Support for firing articles according to claim 2, wherein the two carrier plates (10, 12) are connected at their corners via screw means (18), wherein the screw means (18) retain the tensioning plate (14) in approximate registry with the carrier plates (10, 12).

4. Support for firing articles according to claim 3, wherein the two carrier plates (10, 12) project at their corners beyond the beveled corner edges (30) of the tensioning plate (14) and wherein the tensioning cam (20) is provided on one of the screws (18) between the carrier plates (10, 12) and lying against the edge corner (30) of the tensioning plate (14).

5. Support for firing articles according to claim 1, wherein the tensioning device includes a tensioning cam (20), which is mounted on the carrier plate(s) (10, 12) rotatably about an axis perpendicular to the plane of the plate(s) and which cam contacts one corner of the tensioning plate (14) with its cam circumference (26).

6. Support for firing articles according to claim 5, wherein the cam circumference (26) of the tensioning cam (20) radially increases in the circumference direction in such a manner that the tensioning cam (20) is self-detaining in its respective tensioning positions.

7. Support for firing articles according to claim 1, wherein said support is adapted for supporting dental articles during firing.

8. Support for firing articles according to claim 7, wherein said dental articles are crowns or bridges.

9. Support for firing articles according to claim 1, wherein said support is constructed of a non-oxidizing metal.

* * * * *